United States Patent
Caillat et al.

(10) Patent No.: US 6,630,359 B1
(45) Date of Patent: Oct. 7, 2003

(54) MICRO-SYSTEM WITH MULTIPLE POINTS FOR CHEMICAL OR BIOLOGICAL ANALYSIS

(75) Inventors: Patrice Caillat, Echirolles (FR); Jean-Frédéric Clerc, Le Fontani (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/744,252

(22) PCT Filed: Jul. 30, 1999

(86) PCT No.: PCT/FR99/01900

§ 371 (c)(1), (2), (4) Date: Jan. 31, 2001

(87) PCT Pub. No.: WO00/07728

PCT Pub. Date: Feb. 17, 2000

(30) Foreign Application Priority Data

Jul. 31, 1998 (FR) .............................. 98 09868

(51) Int. Cl.[7] .............................. H01L 21/00; C12Q 1/68
(52) U.S. Cl. .................................. 438/1; 435/6; 422/50
(58) Field of Search .................... 438/1; 435/6; 422/50, 422/100

(56) References Cited

U.S. PATENT DOCUMENTS

| | | | |
|---|---|---|---|
| 5,653,939 A | * | 8/1997 | Hollis et al. .................. 422/50 |
| 5,776,791 A | | 7/1998 | Caillat et al. |
| 6,103,552 A | * | 8/2000 | Lin ............................. 438/113 |

FOREIGN PATENT DOCUMENTS

| | | | |
|---|---|---|---|
| EP | 0 402 917 A | 12/1990 | |
| WO | 93 06237 A | 4/1993 | |
| WO | 96 28538 A | 9/1996 | |

OTHER PUBLICATIONS

Livache et al. "Ploypyrrole DNA Chip on a Silicon Device", Analytical Biochemistry, 255, 188–194 (1998).*

Livache et al. "Polypyrrole DNA Chip on a Silicon Device" Analytical Biochemistry. 255, 188–194 (1998).*

Cosnier, Serge. "Electropolymerization of Amphiphilic Monomers for De, Amperometric Biosensors",. Electroanalysis, 9(12), 1997.*

Cosnier, S.: "Electropolymerlization of amphiphilic monomers for designing amperometric biosensors" Electroanalysis, vol. 9, No. 12, 1997, pp. 894–902, XP002101569.

* cited by examiner

*Primary Examiner*—John F. Niebling
*Assistant Examiner*—Viktor Simkovic
(74) *Attorney, Agent, or Firm*—Oblon, Spivak, McClelland, Maier & Neustadt, P.C.

(57) ABSTRACT

A chemical or biological analysis multi-point micro-system including a structure equipped with micro-wells, each micro-well being intended to receive a reagent coupled with a conductive polymer. Each micro-well includes a reception electrode on which the reagent is fixed by the conductive polymer with which it is coupled. Each micro-well also includes a counter-electrode arranged so as to be able to apply, in a volume of the micro-well, an electric field between its counter-electrode and its reception electrode. The structure further enables the simultaneous connection of all the reception electrodes to a first electric potential and enables the simultaneous connection of all the counter-electrodes to a second electric potential to be able to set up the electric field.

20 Claims, 3 Drawing Sheets

MICRO-SYSTEM WITH MULTIPLE POINTS FOR CHEMICAL OR BIOLOGICAL ANALYSIS

BACKGROUND OF THE INVENTION

1. Field of the Invention

The present invention relates to a chemical or biological analysis multi-point micro-system.

2. Discussion of the Background

Conventional electronics are increasingly used as a link in much more complex systems wherein several functions are integrated. Said systems or micro-systems range from physical sensor applications to the latest developments of "biological" chips.

In the first case, a sensitive cell capable of measuring a physical phenomenon is associated with an integrated circuit capable of processing and using the information. This is the case for air bags in the automotive industry.

In the second case, an integrated circuit undergoes a finish enabling it to be used in a biological medium. This is the case for example of an integrated glucose measuring unit or blood pressure probes.

In all cases, the interface between the field of conventional micro-electronics and that of sensors or biologists is the key element of said micro-systems.

Chemical or biological analysis is in the process of undergoing the miniaturisation revolution related to the use of microtechnologies. When multiple tests can be grouped together on a substrate of a few $mm^2$, the costs are reduced and a once exceptional analysis can be used in a standard fashion.

The demand for systems enabling the chemical or biological analysis with a very large number of points is currently emerging with the appearance of screening in pharmacology and DNA tests in biology.

In the first case, it is necessary to determine on a substrate comprising a large number of wells filled with the same reagent, the effect of different molecules which are deposited selectively in each well in a sequential fashion. In the second case, each well is filled with a different DNA probe and analyte for which the genomic sequence is to be detected is placed in contact during the analysis with all the wells. In analytical chemistry, there is also a significant demand for the miniaturisation of chemical reaction wells.

In terms of producing the wells, depositing the liquids in said wells and result reading and acquisition systems, Research and Development work is significant.

In the field of biological analysis or more generally of pharmacological tests on new molecules, reduction in size is an extremely attractive testing tool from an economic point of view. More specifically, an analysis micro-system can be compared to a structure associating a substrate on which different reagents are first fixed and then placed in the presence of the solution under analysis, and a method used to measure the reactivity obtained. If required, processing in the micro-system itself of the information obtained may be provided for.

There are different techniques for fixing different reagents onto a substrate.

A first technique consists of activating sites where the reagents are then deposited and fixed with various chemical molecules. This technique is essentially used on glass substrates. The reagents are deposited by micro-pipetting or using an ink jet type technique. In chemical terms, to ensure the interface between the substrate and the reagent, substances such as silanes, lysines, thiols may be used when the substrate is coated beforehand with gold. This chemistry is complex, especially for controlling its reproducibility on a substrate that can comprise several thousand different sites. A representative example of this technique is the patent U.S. Pat. No. 5,474,796 which relates to the surface structure: the reagents are fixed onto a substrate comprising hydrophilic zones and hydrophobic zones. For this reason, the matrices obtained are very regular.

According to a second technique applied to the field of DNA chips (the reagent is a DNA probe, particularly an oligonucleotide with around twenty bases), it was proposed to build the probe base by base on each site. The use of successive masking to produce this synthesis in situ is known: each site is coated with a photoprotected base. Photomasking then makes it possible to remove the protection from the sites and attach an additional photoprotected base chemically. The operation is repeated until the required probe is obtained on each site. It is currently possible to build several tens of thousands of different probes on a substrate. This technique is excellent but it cannot be used to obtain probes with a large number of bases (the limit is approximately 20). It is also possible to fix a protected base from the outset not with a photosensitive radical but with a chemically sensitive radical. In this case, it is necessary, by pipetting or with an ink jet type technique, to go locally to the site selected to remove the protections from the existing base and attach an additional base.

A third technique relates to electrodeposition on electrically polarised sites of a conductive polymer carrying the selected reactive species. For this subject refer to the article "Electropolymerization of pyrrole and immobilization of glucose oxidase in a flow system: influence of the operating conditions on analytical performance" by Juan-C. VIDAL et al., published in Biosensors and Biolelectronics, vol. 13, No. 3–4, pages 371–382, 1998. The substrate is connected electrically to the outside and immersed in a tank containing the chemical species to be deposited. The selected site is polarised and copolymerisation is performed (at least one minute at a voltage less than 1 V). Then another solution carrying another reagent is used and another site is polarised on the surface on the substrate and so on. Using this method, different reagents were fixed on different zones of the substrate, thus enabling a multi-point analysis.

An interesting improvement of the last technique consists of integrating the site addressing electronics in the substrate itself. The conductive polymers used for this process are polyanilines, polypyrroles. For this subject, refer to the documents WO 94/22 889, FRA-2741 and FR-A-2 741 476. This method is of interest since the fixation of the probe onto its site is strong, reproducible and well controlled. It is a sequential technique: each site is polarised successively and the substrate is coated completely or immersed in the reagent carrier solution at each passage. However, when the number of sites becomes high, the processing time of each site substrate becomes prohibitive; the longer the copolymerisation time, the longer the time required for rinsing or to introduce a new electrolyte.

The use of these biological probe devices may use a very wide range of methods: impedance-metry electrical measurement, microscales, optical measurement with change of refractive index, radioactive labelling, fluorescence. This last method is increasingly used since it is relatively easy to implement and it shows a good sensitivity. Schematically, it consists of coupling the analyte under test with a fluophor. The analyte is placed in contact with the reagent fixed locally on the micro-system. If there is a reaction/pairing of any kind, the analyte containing the fluophor will remain on the test zone. After washing, reading of the fluorescence will make it possible to determine whether there is pairing on the carrier site.

SUMMARY OF THE INVENTION

To remedy the problems of the prior art, the present invention proposes the use of a structure which is used to fix, in a single electropolymerisation step, reagents coupled with monomers of conductive polymers on sites connected electrically to the outside.

Therefore, the invention relates to a process to produce a chemical or biological analysis multi-point micro-system, comprising steps consisting in:
 a) coupling a reagent with a conductive polymer monomer,
 b) depositing an electrolytic carrier solution containing a mixture of said reagent coupled with said conductive polymer monomer in at least one micro-well of the micro-wells formed on a structure, each micro-well comprising a reception electrode and a counter-electrode, the electrolytic solution being deposited in sufficient quantity to close the electrochemical circuit between the reception electrode and the counter-electrode,
 c) applying an electric field between the reception electrode and the counter-electrode to copolymerise and fix, in the micro-well where the electrolytic solution has been deposited, said conductive polymer with the reagents on the reception electrode,
 d) rinsing the micro-wells of the structure to eliminate the remaining carrier solution.

Steps a), b) and c) may be repeated as many times as required to deposit the different reagents in different micro-wells.

The invention also relates to a chemical or biological analysis multi-point micro-system composed of a structure equipped with micro-wells, each micro-well being intended to receive a reagent coupled with a conductive polymer, each micro-well comprising a reception electrode on which the reagent is fixed by means of the conductive polymer with which it is coupled, each micro-well comprising a counter-electrode arranged so as to be able to apply, in a volume of the micro-well, an electric field between its counter-electrode and its reception electrode, the structure comprising the means enabling the simultaneous connection of all the reception electrodes and means enabling the simultaneous connection of all the counter-electrodes to a second electric potential to be able to set up said electric field.

According to a first alternative, the structure may comprise a passive substrate, one face of which is coated with a first conductive layer itself coated with a first layer of insulating material, the first coat of insulating material comprising said micro-wells showing the first conductive layer which forms said reception electrodes, the first layer of insulating material supporting a second conductive layer forming a common counter-electrode.

According to a second alternative, the structure may comprise an active substrate, one face of which comprises said reception electrodes and is coated with a first layer of insulating material comprising said micro-wells, the base of which corresponds to the reception electrodes, the first layer of insulating material supporting a conductive layer forming a common counter-electrode, multiplexing means being provided to connect all the reception electrodes simultaneously.

A second layer of insulating material may cover the conductive layer forming the counter-electrode to embed it. The second insulating layer may support a conductive layer used as a reference pseudo-electrode.

BRIEF DESCRIPTION OF THE FIGURES

The invention will be understood more clearly and other advantages and specificities will be seen upon reading the following description, given as a non-restrictive example, accompanied by the appended figures wherein.

DESCRIPTION OF THE PREFERRED EMBODIMENTS

To produce the micro-system according to the invention, two cases should be taken into consideration. The structure may comprise a passive substrate, i.e. it does not comprise integrated electronics. In this case, the substrate may be coated with a conductive surface (e.g. metal) itself coated with a layer of material providing electrical insulation and wherein the micro-cavities are formed. Said micro-cavities open locally onto the conductive surface. In this case, the uncovered zones of the conductive surface form the reception electrodes.

The substrate may also be active, in which case the integrated electronics may be used for different functions: localised site heating, local pH measurements, fluorescence signal reading, etc. In most cases, it is not possible to allow the sites to short-circuit for subsequent functions which must remain addressable on each site independently of the others. The multiplexing required for these functions may then be used during the micro-system production process. It is indeed possible to address all the sites collectively to perform the reagent fixing operation. Each site may subsequently be addressed individually.

FIGS. 1A to 1H are transverse and partial section views. They illustrate a first embodiment of a micro-system according to the invention for which the counter-electrode is located on the surface and for which the substrate is passive.

Figure 1A:
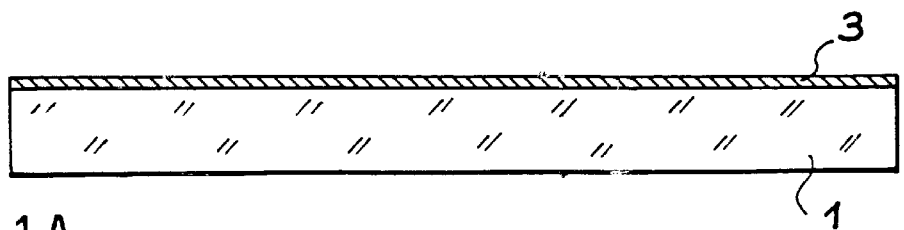
FIGS. 1A to 1H represent different steps of a process to produce a chemical or biological analysis multi-point micro-system according to the present invention.
Figure 1B:
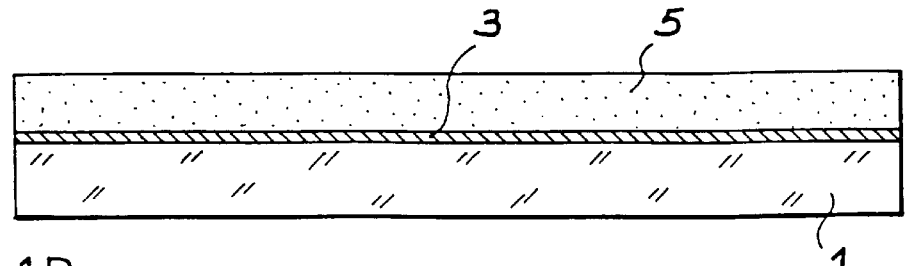

FIG. 1A represents a substrate 1 composed of a parallelepiped plate which may be made of a material such as glass, silicon or plastic. On the main face of this plate, a metal layer 3, for example chromium, gold or platinum, of a thickness between 0.1 and 10 µm has been deposited. As shown in FIG. 1B, on the metal layer 3, a photosensitive polymer film 5, for example a polyimide film of a thickness between 1 and 50 µm has been deposited.

Figure 1C:
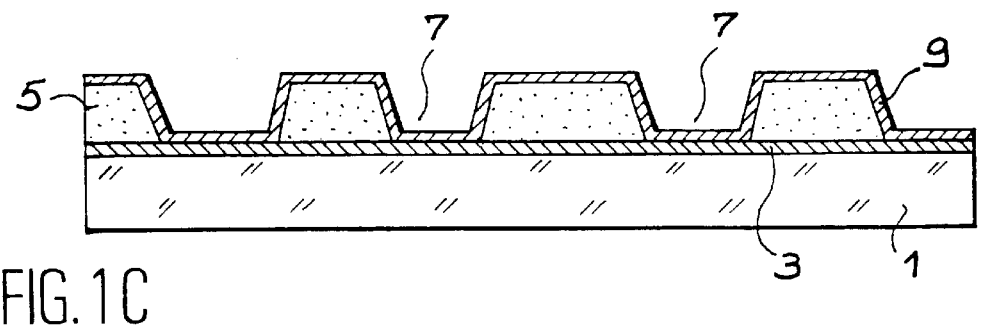

Micro-wells 7 are then formed by insolation and development of the polyimide film (see FIG. 1C). They are advantageously formed with sloping sides. The micro-wells formed detect locally the metal layer 3. A new metal layer 9 is then deposited uniformly on the polyimide film including inside the micro-wells 7. The metal layer 9 may be made of chromium, gold or platinum and be 0.1 to 10 µm thick.

Figure 1D:
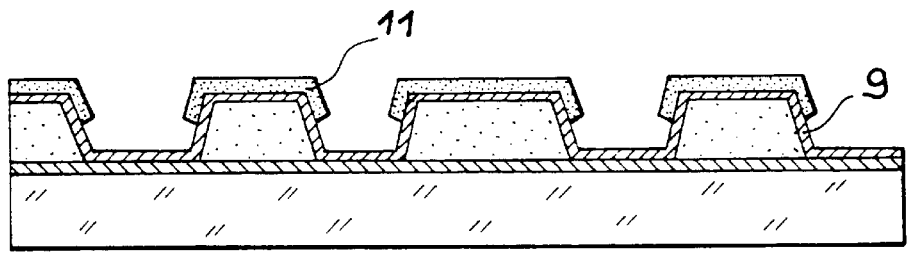

As shown in FIG. 1D, a layer of masking resin 11 is deposited on the metal layer 9 and the zones to be engraved in said metal layer 9 are defined.

Figure 1E:
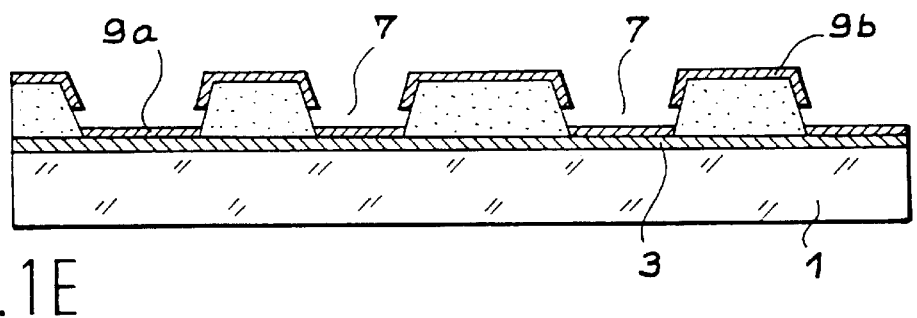

The metal layer 9 is then engraved at the accessible positions and the resin 11 is removed. The structure represented in FIG. 1E is obtained. Each micro-well 7 comprises at its base an electrode 9a, all the electrodes 9a being connected electrically by means of the metal layer 3. A common electrode 9b covers the upper face of the polymer film 5.

Figure 1F:
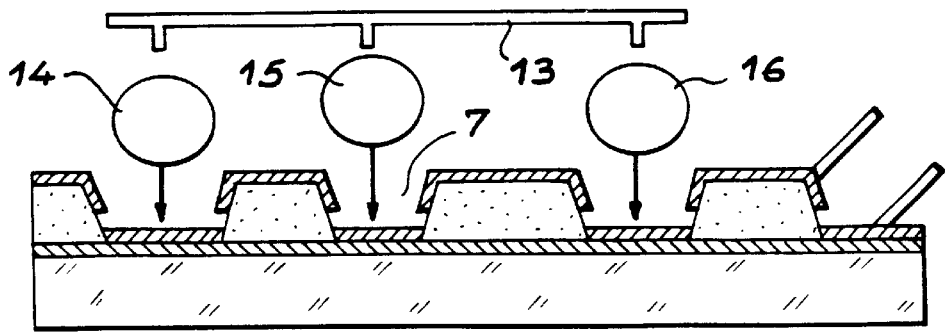

Using a micro-fluid technique (micro-capillary, fountain pen, ink jet type printing head, etc.), a solution carrying a reagent is deposited in each micro-well. FIG. 1F shows a distribution system, represented schematically under the reference 13, supplying in each micro-well 7 a drop 14, 15, 16 of an electrolytic solution carrying a mixture of specific reagent coupled with a monomer and a single monomer.

Figure 1G:
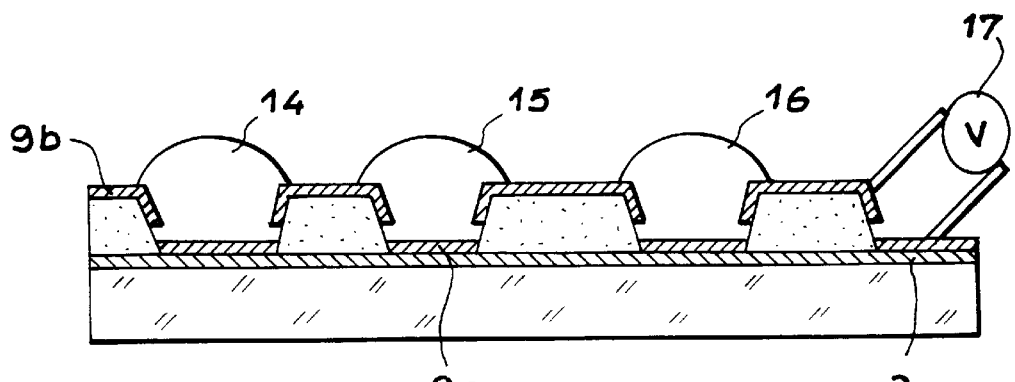
Figure 1H:
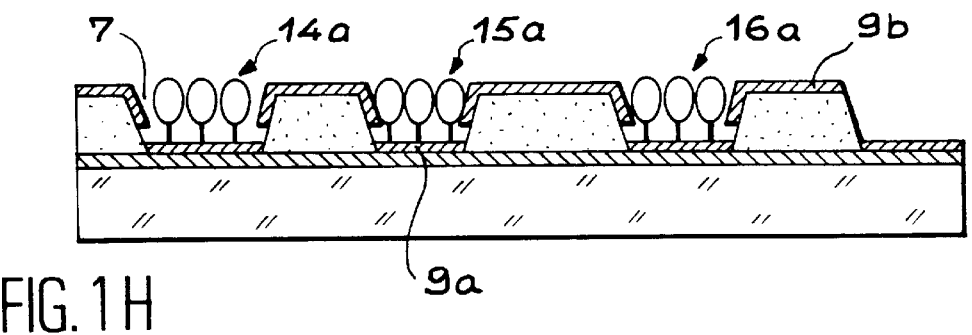

FIG. 1G shows the drops 14, 15, 16 of electrolytic solutions arranged in micro-wells. The micro-wells prevent the mixture of different solutions. The quantities of electrolytic solutions are such that they close the electrochemical circuit between the electrodes 9a and the counter-electrode 9b.

By applying an appropriate electric field supplied by a voltage generator 17 connected between the metal layer 3 and the counter-electrode 9b, copolymerisation and fixation of the conductive polymers onto the electrodes 9a are obtained.

The micro-wells 7 are then rinsed to obtain, in each micro-well, a reagent 14a, 15a, 16a fixed to an electrode 9a by a conductive polymer carrying the reagent.

Figure 2:
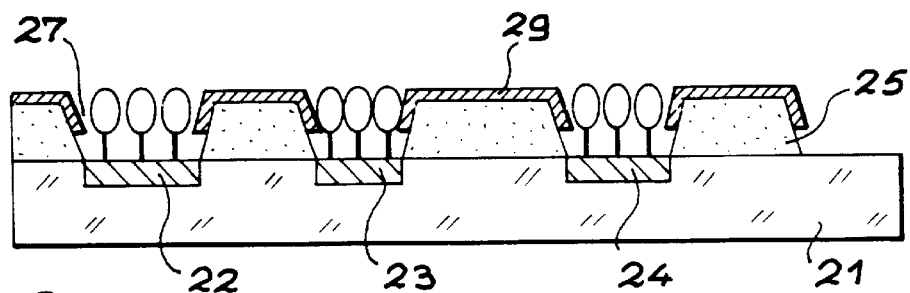
FIG. 2 represents an alternative chemical or biological analysis multi-point micro-system according to the present invention.

If the substrate is active, the reception electrodes of the reagent cannot generally be continuously connected to a common conductive layer. In this case, as represented in FIG. 2, the substrate 21 is equipped at the outside with reception electrodes 22, 23, 24 insulated electrically from each other as a general rule but which may be, by means of a multiplexing system, connected collectively to one of the terminals of a voltage generator. The rest of the structure is similar to the structure described above: photosensitive polymer film 25 wherein micro-wells 27 are formed and supporting a counter-electrode 29.

Figure 3A:
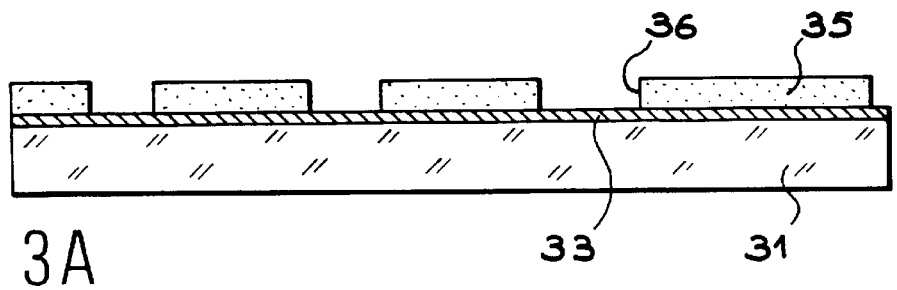
FIGS. 3A to 3C illustrate the steps of another process to produce a chemical or biological analysis multi-point micro-system according to the present invention.
Figure 3B:
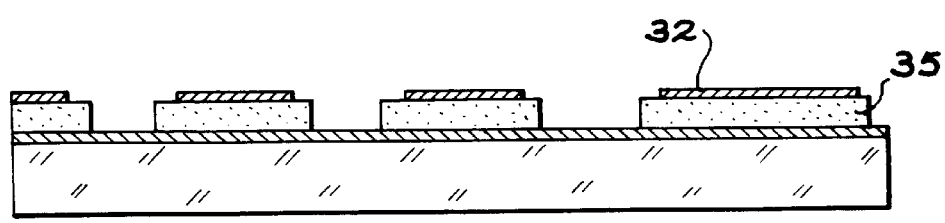
Figure 3C:
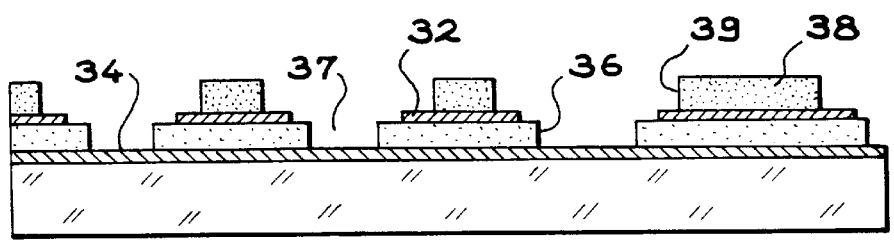

FIGS. 3A to 3C illustrate the production of another alternative for which the counter-electrode is embedded. The contact between the electrolytic solution and the reception electrodes is performed as above either with reception electrode connected continuously to a common conductive layer, or with reception electrodes insulated electrically from each other but which can be addressed simultaneously by multiplexing. For example, FIGS. 3A to 3C illustrate the case where the reception electrodes are connected continuously to a common conductive layer. The first steps of the process are similar to those illustrated in FIGS. 1A and 1B and, for this reason, are not represented.

FIG. 3A shows the substrate 31 coated with the metal layer 33 and the photosensitive polymer film 35 which has undergone photolithography and engraving, thus revealing the metal layer 33 at the base of holes 36 produced in the film 35.

A metal layer, for example chromium, gold or platinum, of a thickness between 0.1 and 10 $\mu$m, is then deposited on the top face of the structure. This layer undergoes photolithography and engraving to leave zones 32 on the film 35, said zones 32 forming the counter-electrode (see FIG. 3B).

Another layer of polymer 38 is then deposited and engraved to complete the micro-wells. The engraving forms holes 39 centred on the holes 36 and of a larger diameter. They allow the counter-electrode 32 to overflow into the micro-wells 37 (see FIG. 3C). The metal-coated base 34 of a micro-well forms a reception electrode for the microsystem.

The structure obtained may then be treated as above to receive the planned reagents. This structure offers improved contact between the electrolyte and the counter-electrode.

Figure 4:
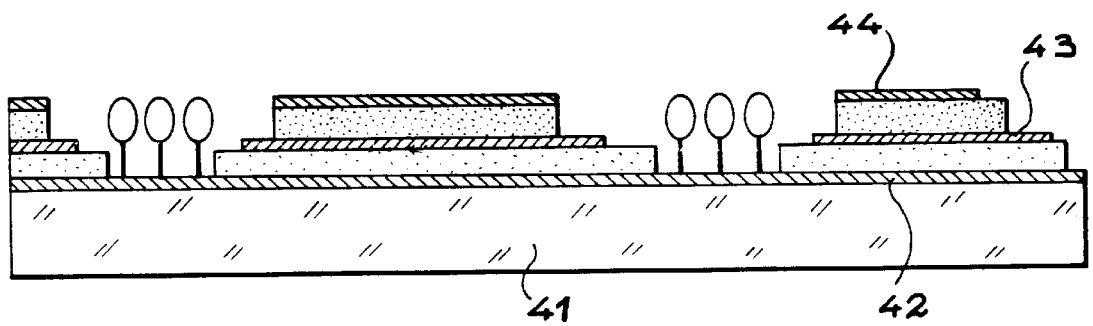
FIG. 4 represents another alternative chemical or biological analysis multi-point micro-system according to the present invention.

An alternative to the structure which has just been described consists of introducing a third electrode on the surface to be used as a reference. It may consist of an absolute reference (with a gel) or a pseudo-reference (for example Ti/TiO$_2$). The cell formed then comprises a reception electrode, a counter-electrode and a reference electrode. This solution is represented in FIG. 4 which shows: a substrate 41 (passive in this example), a conductive surface 42 supplying the reception electrodes locally, the counter-electrode 43 and the reference electrode 44. The metal surfaces can, of course, be inverted and the counter-electrode left on the surface and the reference electrode on the intermediate level.

The invention offers the advantage of the simplicity of the deposition of electrolytic solutions with a fluid logic technique. It enables a particularly sturdy and chemical neutral fixation method due to the monomer copolymerisation. A large number of reagents may be easily introduced since the copolymerisation and fixation operation is collective. The monomers may be coupled with numerous types of chemical and biological substances (glucose oxidase, antigens, DNA probes, etc.).

The solution offered by the invention is compatible with the in situ synthesis of nucleic probes using a chemical process described at the start of the disclosure. The first base is fixed by electrocopolymerisation and the subsequent construction is conducted chemically. Polypyrrole is in this case a good candidate due to its high chemical stability. This fixation method is attractive since it is very robust in comparison to fixations with silanisation, for example.

This technique also offers the advantage of being compatible with the use of active substrates by using the integrated electronic function for the collective electrocopolymerisation and fixation step.

What is claimed is:

1. A process to produce a chemical or biological analysis multipoint micro-system, comprising steps of:

providing a plurality of micro-wells each configured to receive a reagent coupled with a conductive copolymer, each of the plurality of micro-wells including a reception electrode on which the reagent is to be fixed by the conductive polymer, and a counter-electrode positioned to apply an electric field between the counter-electrode and reception electrode sufficient to copolymerize and fix said conductive polymer with the reagent on the reception electrode, means for simultaneously connecting all the reception electrodes, and means for simultaneously connecting all the counter-electrodes to a second electric potential to set up said electric field;

coupling the reagent with the conductive polymer monomer;

depositing an electrolytic carrier solution containing a mixture of said reagent coupled with said conductive polymer monomer in at least one micro-well of the plurality of micro-wells;

applying an electric field between the reception electrode and the counter-electrode to copolymerise and fix, in the micro-well where the electrolytic solution has been deposited, said conductive polymer with the reagents on the reception electrode; and rinsing the micro-wells of the structure to eliminate the remaining carrier solution.

2. A process according to claim 1, wherein the coupling, depositing and applying steps are repeated as many times as required to deposit the different reagents in different micro-wells.

3. A chemical or biological analysis multi-point micro-system comprising:

a plurality of micro-wells each configured to receive a reagent coupled with a conductive copolymer, each of the plurality of micro-wells including a reception electrode on which the reagent is to be fixed by the conductive polymer, and a counter-electrode positioned to apply an electric field between the counter-electrode and reception electrode sufficient to copolymerize and fix said conductive polymer with the reagent on the reception electrode;

means for simultaneously connecting all the reception electrodes; and means for simultaneously connecting all the counter-electrodes to a second electric potential to set up said electric field.

4. A chemical or biological analysis multi-point micro-system according to claim 3, wherein the structure comprises a passive substrate, one face of which is coated with a first conductive layer itself coated with a first layer of insulating material, the first coat of insulating material comprising said micro-wells revealing the first conductive layer which forms said reception electrodes, the first layer of insulating material supporting a second conductive layer forming a common counter-electrode.

5. A chemical or biological analysis multi-point micro-system according to claim 3, wherein the structure comprises an active substrate, one face of which comprises said reception electrodes and is coated with a first layer of insulating material comprising said micro-wells, the base of which corresponds to the reception electrodes, the first layer of insulating material supporting a conductive layer forming a common counter-electrode, multiplexing means being provided to connect all the reception electrodes simultaneously.

6. A chemical or biological analysis multi-point micro-system according to claims 4, wherein a second layer of insulating material covers the conductive layer forming the counter-electrode to embed it.

7. A chemical or biological analysis multi-point micro-system according to claim 6, wherein the second layer of insulating material supports a conductive layer used as a reference pseudo-electrode.

8. A chemical or biological analysis multi-point micro-system according to claim 5, wherein a second layer of insulating material covers the conductive layer forming the counter-electrode to embed it.

9. A chemical or biological analysis multi-point micro-system according to claim 8, wherein the second layer of insulating material supports a conductive layer used as a reference pseudo-electrode.

10. A chemical or biological analysis multi-point micro-system comprising:

a substrate;

a plurality of micro-wells formed on the substrate and each configured to receive a reagent coupled with a conductive polymer, each of the micro-wells including a reception electrode and a counter-electrode positioned to generate an electric field between the counter-electrode and reception electrode sufficient to copolymerize and fix said conductive polymer with the reagent on the reception electrode;

first connecting means for connecting all of the reception electrodes simultaneously; and second connecting means for connecting all of the counter-electrodes simultaneously to a second electric potential to set up the electric field.

11. A chemical or biological analysis micro-system according to claim 10, wherein:

the substrate comprises a passive substrate, one face of which is coated with a first conductive layer coated with a first layer of insulating material;

the first layer of insulating material forms said micro-wells revealing the first conductive layer and supports a second conductive layer forming a common counter-electrode; and the first conductive layer forms said reception electrodes.

12. A chemical or biological analysis micro-system according to claim 10, wherein:

the substrate comprises an active substrate, one face of which comprises said reception electrodes and is coated with a first layer of insulating material;

the first layer of insulating material forms said micro-wells and supports a conductive layer forming a common counter-electrode;

the reception electrodes forms bases of said micro-wells, respectively; and the first connecting means is multiplexing means provided to connect all of the reception electrodes simultaneously.

13. A chemical or biological analysis micro-system according to claims 11, further comprising a second layer of insulating material covering and embedding the conductive layer forming the counter-electrode.

14. A chemical or biological analysis micro-system according to claim 13, wherein the second layer of insulating material is configured to support a conductive layer for a reference pseudo-electrode.

15. A chemical or biological analysis micro-system according to claim 12, further comprising a second layer of insulating material covering and embedding the conductive layer forming the counter-electrode.

16. A chemical or biological analysis micro-system according to claim 15, wherein the second layer of insulating material is configured to support a conductive layer for a reference pseudo-electrode.

17. A chemical or biological analysis micro-system according to claim 11, wherein the first layer of insulating material comprises a photosensitive polymer film.

18. A chemical or biological analysis micro-system according to claim 12, wherein the first layer of insulating material comprises a photosensitive polymer film.

19. A chemical or biological analysis micro-system according to claim 11, wherein the first and second conductive layers comprise a metal selected from the group consisting of chromium, gold, and platinum.

20. A chemical or biological analysis micro-system according to claim 12, wherein the conductive layer comprises a metal selected from the group consisting of chromium, gold, and platinum.

* * * * *